United States Patent
Hollyer et al.

(10) Patent No.: US 10,314,726 B2
(45) Date of Patent: Jun. 11, 2019

(54) STENT WITH COATED STRUTS

(71) Applicant: BOSTON SCIENTIFIC SCIMED, INC., Maple Grove, MN (US)

(72) Inventors: Matthew B. Hollyer, Williamstown, VT (US); Man Minh Nguyen, Harvard, MA (US); Sean P. Fleury, Brighton, MA (US); Jason Weiner, Grafton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 82 days.

(21) Appl. No.: 15/260,582

(22) Filed: Sep. 9, 2016

(65) Prior Publication Data

US 2017/0071767 A1   Mar. 16, 2017

Related U.S. Application Data

(60) Provisional application No. 62/216,573, filed on Sep. 10, 2015.

(51) Int. Cl.
| | |
|---|---|
| *A61F 2/06* | (2013.01) |
| *A61F 2/91* | (2013.01) |
| *A61F 2/86* | (2013.01) |
| *A61L 31/10* | (2006.01) |

(52) U.S. Cl.
CPC ............... *A61F 2/91* (2013.01); *A61F 2/86* (2013.01); *A61L 31/10* (2013.01); *A61F 2210/0076* (2013.01); *A61F 2250/0024* (2013.01); *A61F 2310/00011* (2013.01)

(58) Field of Classification Search
CPC ...... A61F 2/82; A61F 2/86; A61F 2/07; A61F 2/90; A61F 2002/072; A61F 2250/0024; A61F 2250/003
See application file for complete search history.

(56) References Cited

U.S. PATENT DOCUMENTS

| | | | |
|---|---|---|---|
| 5,876,448 | A | 3/1999 | Thompson et al. |
| 6,176,875 | B1 | 1/2001 | Lenker et al. |
| 7,637,942 | B2 | 12/2009 | Mangiardi et al. |
| 8,435,286 | B2 | 5/2013 | Brister |
| 8,764,813 | B2 | 7/2014 | Jantzen et al. |
| 8,784,473 | B2 | 7/2014 | Tupil et al. |
| 8,834,559 | B2 | 9/2014 | Mailander et al. |
| 8,926,688 | B2 | 1/2015 | Burkart et al. |

(Continued)

FOREIGN PATENT DOCUMENTS

WO      1997025002 A1    7/1997

*Primary Examiner* — Brian A Dukert
(74) *Attorney, Agent, or Firm* — Seager, Tufte & Wickhem, LLP

(57) ABSTRACT

A medical stent may include a tubular support structure including a plurality of struts defining a plurality of cells disposed between the plurality of struts. A polymeric coating may be disposed over the tubular support structure such that a first portion of the plurality of cells are closed by the polymeric coating in a first region of the tubular support structure and a second portion of the plurality of cells in a second region of the tubular support structure remain open to fluid flow and/or tissue ingrowth therethrough. The struts in the first region of the tubular support structure and the struts in the second region of the tubular support structure may be at least partially covered by the polymeric coating.

20 Claims, 14 Drawing Sheets

(56) References Cited

U.S. PATENT DOCUMENTS

| | | |
|---|---|---|
| 9,345,600 B2 | 5/2016 | Jantzen et al. |
| 9,345,601 B2 | 5/2016 | Jantzen et al. |
| 2005/0087520 A1 | 4/2005 | Wang et al. |
| 2005/0228482 A1 | 10/2005 | Herzog et al. |
| 2006/0217799 A1 | 9/2006 | Mailander et al. |
| 2007/0067015 A1 | 3/2007 | Jones et al. |
| 2007/0219619 A1 | 9/2007 | Dieck et al. |
| 2010/0063579 A1 | 3/2010 | An |
| 2010/0161033 A1 | 6/2010 | Jantzen et al. |
| 2011/0319980 A1* | 12/2011 | Ryan .................. A61F 2/07 623/1.16 |
| 2016/0235895 A1 | 8/2016 | Costello |

* cited by examiner

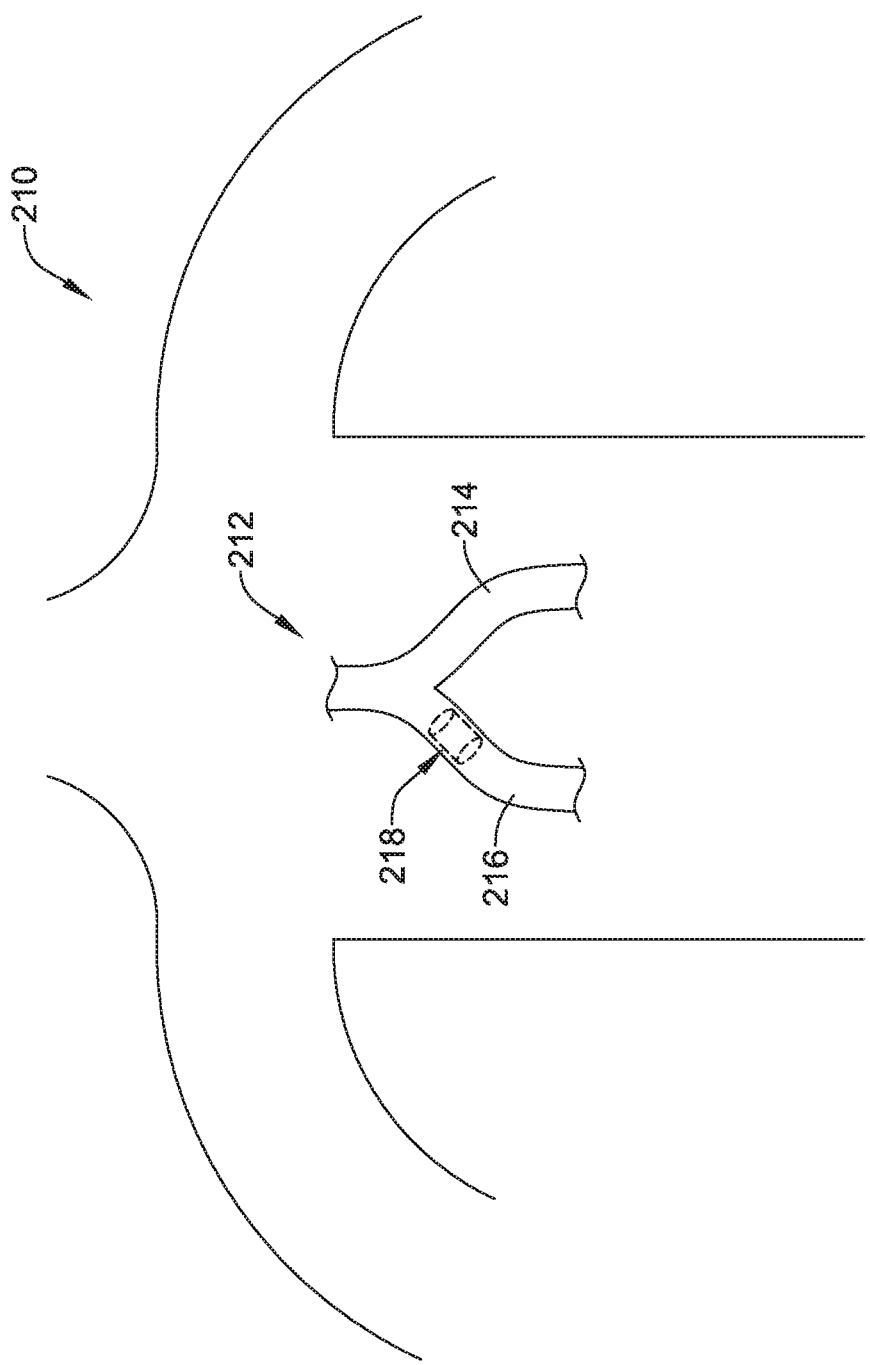

STENT WITH COATED STRUTS

CROSS-REFERENCE TO RELATED APPLICATIONS

This application claims priority under 35 U.S.C. § 119 to U.S. Provisional Application Ser. No. 62/216,573, filed Sep. 10, 2015, the entire disclosure of which is incorporated herein by reference.

TECHNICAL FIELD

The disclosure is directed to an endoprosthesis, such as a stent. More particularly, the disclosure is directed to a stent that includes cushioned struts that reduce irritation while permitting fluid flow.

BACKGROUND

An endoprosthesis may be configured to be positioned in a body lumen for a variety of medical applications. For example, an endoprosthesis may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. In some instances, an endoprosthesis may be used within an organ such as the pancreas, in the biliary system or in the pulmonary system. In some cases, there can be a desire to retain patency within a main lumen while not blocking fluid flow from side branches feeding into or out of the main lumen. In some cases, there can be a desire to provide endoprostheses that exhibit anti-migration features, while reducing the trauma to the body lumen of the patient if removal of the endoprosthesis is desired. In some cases, there can be a desire to avoid tissue irritation that can occur in response to a bare metal stent or stent component contacting tissue.

Accordingly, it is desirable to provide endoprostheses that can retain patency within a main lumen within the body structure while not blocking fluid flow from side branches within the body structure, while providing anti-migration features, and/or while avoiding tissue irritation.

BRIEF SUMMARY

The disclosure is directed to several alternative designs, materials and methods of manufacturing medical device structures and assemblies, and uses thereof.

A medical stent is disclosed. The medical stent includes a tubular support structure including a plurality of struts. The plurality of struts define a plurality of cells disposed between the plurality of struts. A polymeric coating is disposed over the tubular support structure such that a first portion of the plurality of cells are closed by the polymeric coating in a first region of the tubular support structure and a second portion of the plurality of cells in a second region of the tubular support structure remain open to fluid flow therethrough. The struts in the first region of the tubular support structure and the struts in the second region of the tubular support structure are at least partially covered by the polymeric coating.

Alternatively or additionally to any of the embodiments above, the struts in the first region of the tubular support structure and the struts in the second region of the tubular support structure are encapsulated by the polymeric coating.

Alternatively or additionally to any of the embodiments above, the polymeric coating is formed by covering the tubular support structure with the polymeric coating and subsequently removing part of the polymeric coating spanning one or more of the plurality of cells within the second region of the tubular support structure.

Alternatively or additionally to any of the embodiments above, the polymeric coating is formed by encapsulating the plurality of struts and subsequently coating at least one or more of the plurality of cells within the first region of the tubular support structure.

Alternatively or additionally to any of the embodiments above, the polymeric coating is formed by placing the tubular support structure over a mandrel and then spray coating the tubular support structure, wherein the mandrel includes raised portions contacting the tubular support structure within the first region and portions spaced from the tubular support structure within the second region.

Alternatively or additionally to any of the embodiments above, the first region of the tubular support structure, in which the first portion of the plurality of cells are covered by the polymeric coating, includes one or more distinct areas of the tubular support structure.

Alternatively or additionally to any of the embodiments above, the second region of the tubular support structure, in which the second portion of the plurality of cells remain open to fluid flow therethrough, includes one or more distinct areas of the tubular support structure.

Alternatively or additionally to any of the embodiments above, the second region of the tubular support structure, in which the second portion of the plurality of cells remain open to fluid flow therethrough, spans over half of the tubular support structure.

Alternatively or additionally to any of the embodiments above, the polymeric coating comprises polyurethane or silicone.

Alternatively or additionally to any of the embodiments above, the medical stent comprises a pulmonary stent.

Alternatively or additionally to any of the embodiments above, the medical stent comprises an esophageal stent.

Alternatively or additionally to any of the embodiments above, the medical stent comprises a pancreatic stent.

A medical stent is disclosed. The medical stent includes a metallic support structure including a plurality of struts. The plurality of struts together defining a shape of the metallic support structure. A cushioning material is disposed on at least some of the plurality of struts. At least some of the inter-strut spaces adjacent struts bearing the cushioning material are open to fluid flow therethrough.

Alternatively or additionally to any of the embodiments above, the medical stent further comprises a polymeric layer spanning at least some of the inter-strut spaces that are different inter-strut spaces than those that are open to fluid flow.

Alternatively or additionally to any of the embodiments above, the cushioning material comprises a polymeric material, and the polymeric layer comprises the same polymeric material.

Alternatively or additionally to any of the embodiments above, the cushioning material comprises polyurethane or silicone.

A method of manufacturing a medical stent is disclosed. The method comprises coating a tubular support structure including a plurality of struts defining a plurality of inter-strut spaces with a polymeric coating such that the plurality of struts and the plurality of inter-strut spaces are covered with the polymeric coating; and selectively removing the polymeric coating from at least some of the inter-strut spaces such that a portion of at least some of the inter-strut spaces are opened but the plurality of struts remain covered by the polymeric coating.

Alternatively or additionally to any of the embodiments above, selectively removing the polymeric coating comprises using laser ablation.

Alternatively or additionally to any of the embodiments above, the polymeric coating comprises polyurethane or silicone.

Alternatively or additionally to any of the embodiments above, coating a tubular support structure comprises spray coating a tubular support structure.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which:

FIG. 14 is a schematic illustration of a patient, showing a pulmonary stent disposed within the patient's trachea in accordance with an embodiment of the disclosure.

Figure 1:
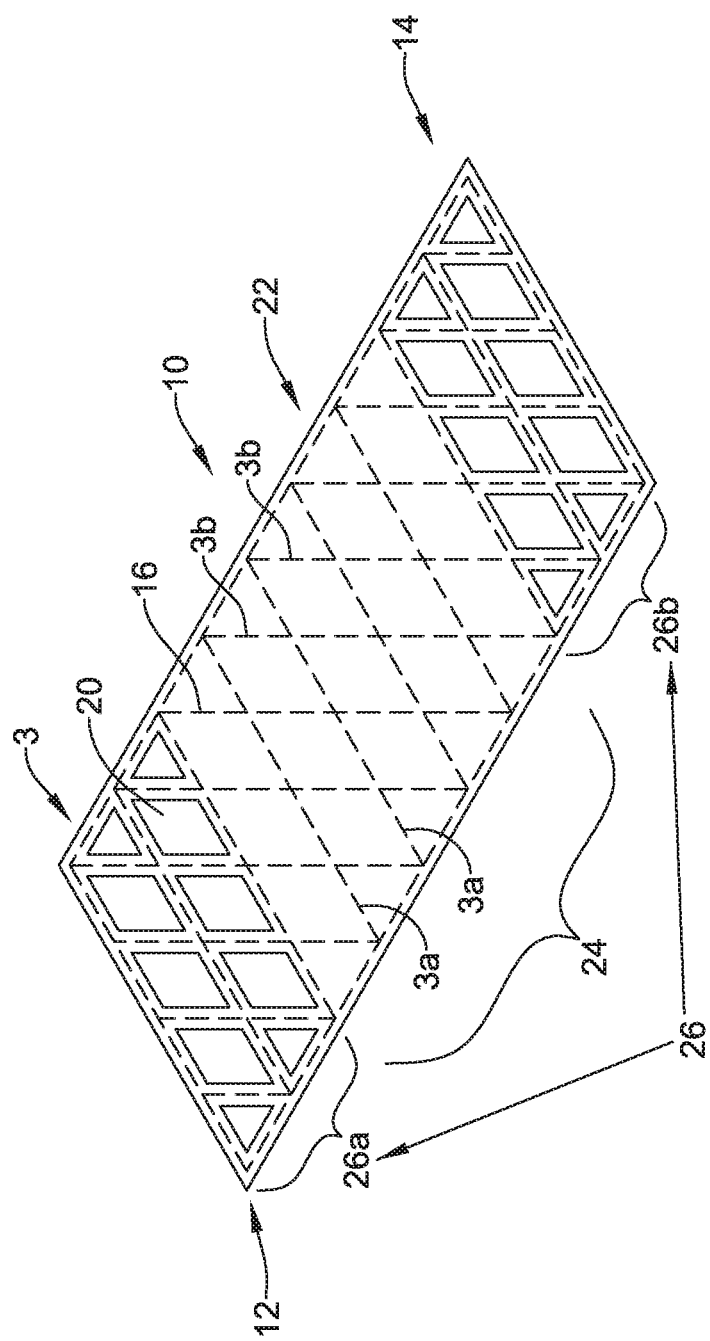
FIG. 1 is a schematic illustration of an endoprosthesis in accordance with an embodiment of the disclosure.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 is a schematic illustration of an endoprosthesis 10 extending from a first end 12 to a second end 14. It will be appreciated that reference to first and second ends is arbitrary, as the endoprosthesis 10 may be deployed in any desired or particular orientation. In some cases, as illustrated, the endoprosthesis 10 may include a tubular support structure 1 that includes a plurality of struts 3. In some cases, the plurality of struts 3 include a first plurality of struts 3a generally extending in a first direction and a second plurality of struts 3b generally extending in a second direction that is different from the first direction. In some cases, the first direction and the second direction may about 90 degrees apart. In some instances, the first direction and the second direction may be less than 90 degrees apart. In some cases, the first direction and the second direction may be more than 90 degrees apart. While illustrated as a woven structure, the tubular support structure 1 may instead be a braided structure, a knitted structure, or a unitary structure formed from a tube, such as a laser cut tubular structure. In some embodiments, the tubular support structure 1 may be a metallic structure, but this is not required in all cases. As can be seen, the plurality of struts 3 together define a plurality of cells or inter-strut spaces 20 between adjacent struts 3.

In some cases, as illustrated, at least part of the endoprosthesis 10 may include a polymeric coating 22. The tubular support structure 1 may be considered as including a first region 24 in which the polymeric coating 22 spans or at least substantially covers the cells 20 that are within the first region 24. The tubular support structure 1 also includes a second region 26 in which the polymeric coating 22 does not span or completely cover the cells 20 that are within the second region 26 and thus the cells 20 within the second region 26 are configured to permit fluid flow therethrough and/or tissue ingrowth once the endoprosthesis 10 has been implanted. As illustrated, the second region 26 may be seen to include a first area 26a that is located near the first end 12 of the endoprosthesis 10 and a second area 26b that is located near the second end 14 of the endoprosthesis 10. As can be seen, the polymeric coating 22 covers the struts 3 within the first region 24 and the second region 26. In some cases, the polymeric coating 22 may be considered as encapsulating the struts 3. In some instances, the polymeric coating 22 encapsulating or otherwise covering the struts 3 may be considered as a cushioning material that can reduce tissue irritation once implanted. In some cases, the polymeric coating 22 may include silicone or polyurethane, although other polymeric materials are contemplated.

Figure 2:
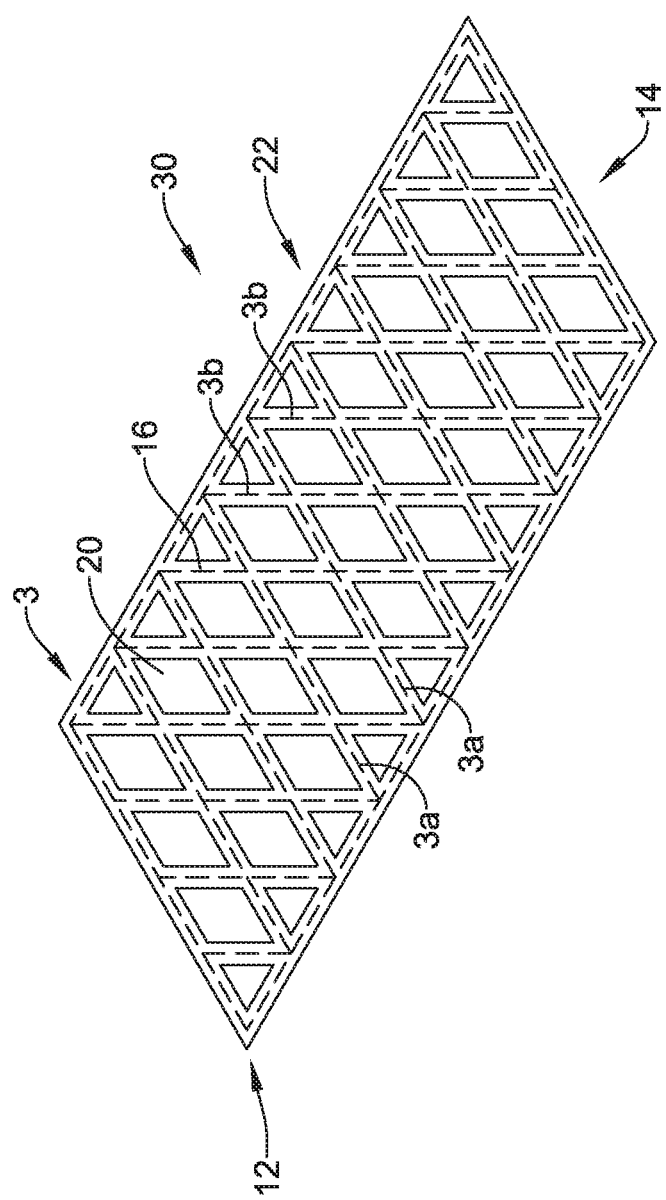
FIG. 2 is a schematic illustration of an endoprosthesis in accordance with an embodiment of the disclosure.

In FIG. 1, the endoprosthesis 10 has a single first region 24 in which the cells 20 are covered by the polymeric coating 22 and second regions 26a, 26b in which the cells 20 are not covered by the polymeric coating 22 and as a result fluid is able to flow through the cells 20 within the second regions 26a, 26b. FIG. 2 illustrates an endoprosthesis 30 in which the struts 3 are encapsulated or otherwise covered by the polymeric coating 22 but all or virtually all of the cells 20 are not covered. FIG. 2 illustrates an embodiment of the endoprosthesis 30 that may be considered as providing good cushioning or protection against tissue irritation while maximizing possible fluid flow through the cells 20.

Figure 3:
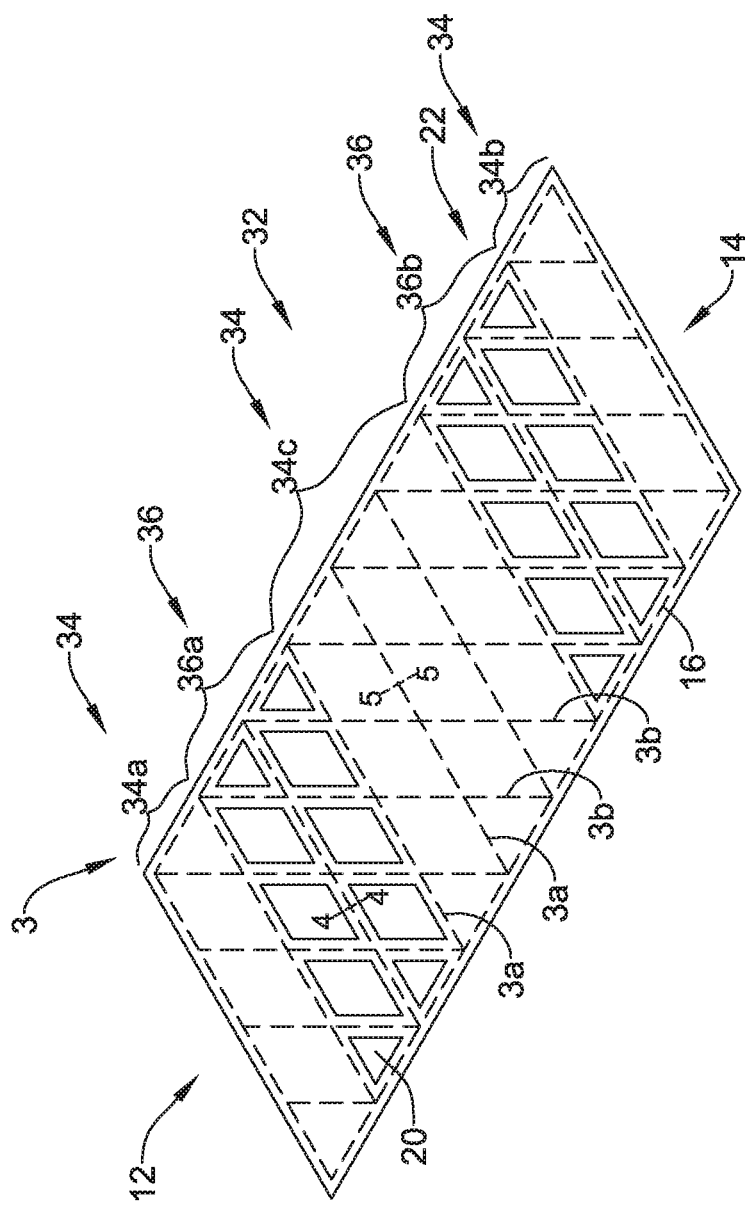
FIG. 3 is a schematic illustration of an endoprosthesis in accordance with an embodiment of the disclosure.

FIG. 3 shows an endoprosthesis 32 in which the tubular support member 1 includes a first region 34 in which the cells 20 are covered by the polymeric coating 22 and a second region 36 in which the cells 20 are not covered by the polymeric coating 22, although the struts 3 within the first region 34 and the second region 36 are covered by the polymeric coating 22. As illustrated, the first region 34 includes an area 34a near the first end 12, an area 34b near the second end 14 and an area 34c that is located in between the area 34a and the area 34b. It will be appreciated that having the first region 34 divided into distinct areas 34a and 34b is merely illustrative, as the endoprosthesis 32 may include any number of distinct areas in which the polymeric coating 22 spans or otherwise covers the cells 20 within distinct areas. Similarly, having the second region 36 divided into distinct areas 36a, 36b and 36c is merely illustrative. Moreover, the relative size and/or shape of the first region 34 and/or the second region 36 may be adjusted as desired or appropriate for a given end use.

Figure 4B:
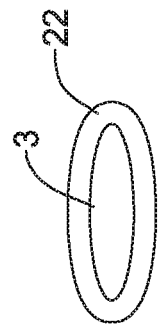
FIGS. 4A and 4B are schematic cross-sectional views taken along line 4-4 of FIG. 3.
Figure 4A:
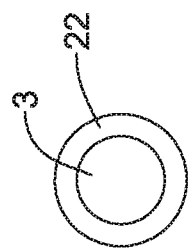

FIGS. 4A and 4B are cross-sectional views taken along line 4-4 of FIG. 3, showing a cross-section through a single strut 3. FIG. 4A shows an embodiment in which the strut 3 has a circular or substantially circular cross-sectional profile while FIG. 4B shows an embodiment in which the strut 3 has an elongate profile. In either case, it can be seen that the polymeric coating 22 encapsulates the strut 3 but does not substantially extend in either direction beyond the strut 3. It will be appreciated that the cells 20 in either side of the strut 3 shown in FIGS. 4A and 4B would be open to fluid flow and/or tissue ingrowth, as can be seen in FIG. 3.

Figure 5A:
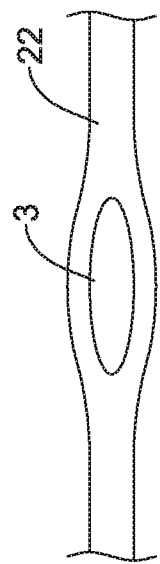
FIGS. 5A and 5B are schematic cross-sectional views taken along line 5-5 of FIG. 3.
Figure 5B:
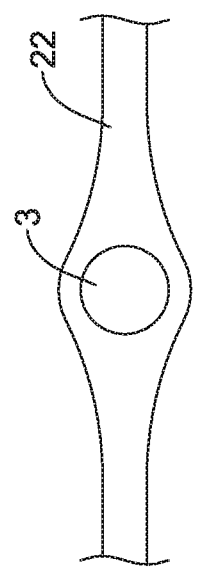

FIGS. 5A and 5B are cross-sectional views taken along line 5-5 of FIG. 3, showing a cross-section through a single strut 3. FIG. 5A shows an embodiment in which the strut 3 has a circular or substantially circular cross-sectional profile while FIG. 5B shows an embodiment in which the strut 3 has an elongate profile. In either case, it can be seen that the polymeric coating 22 encapsulates the strut 3 and extends to either side from the strut 3 as the polymeric coating 22 covers or otherwise spans the cells 20 on either side of the strut 3. It will be appreciated that the cells 20 in either side of the strut 3 shown in FIGS. 5A and 5B would be closed to fluid flow and/or tissue ingrowth, as can be seen in FIG. 3.

Figure 6:
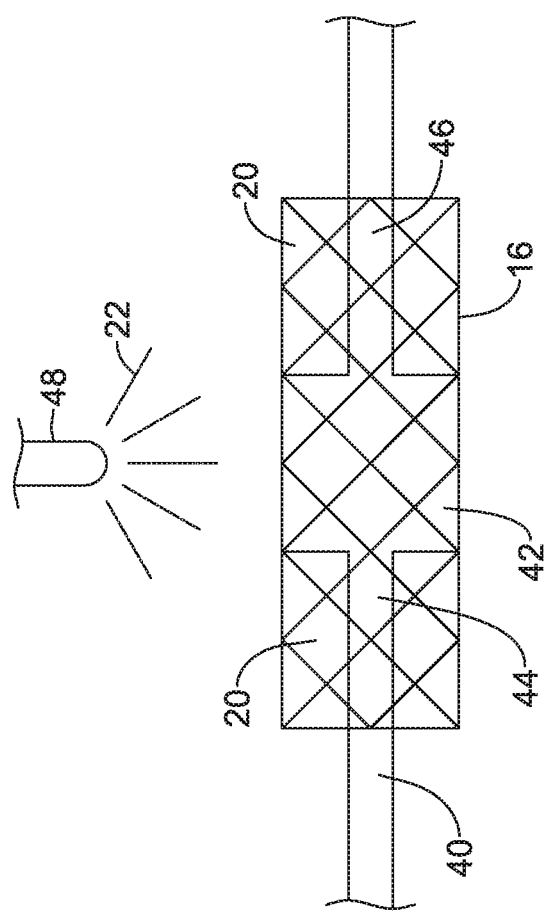
FIG. 6 is a schematic illustration of a system for coating an endoprosthesis utilizing a mandrel for selective coating in accordance with an embodiment of the disclosure.
Figure 7:
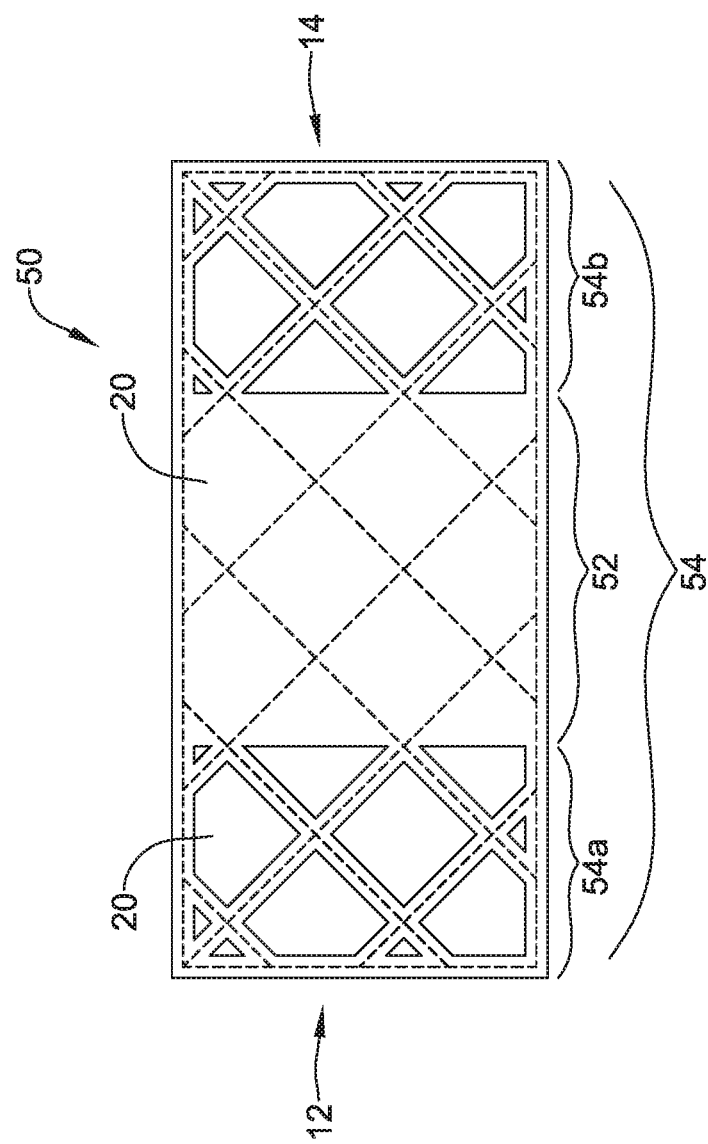
FIG. 7 is a schematic illustration of an endoprosthesis that was coated using the system of FIG. 6, in accordance with an embodiment of the disclosure.

The selective polymeric coatings shown in FIGS. 1-3 may be formed using a variety of techniques and methods. In some cases, the polymeric material may be selectively added where desired, and not added where not wanted. In some cases, the tubular support structure may be coated with the polymeric material, and the polymeric material may be selectively removed where not wanted. FIG. 6 illustrates an embodiment in which material is selectively added. In FIG. 6, a tubular support member 1 is shown. A mandrel 40 may be inserted into the tubular support member 1. As can be seen, the mandrel 40 may include an enlarged diameter portion 42 that has a diameter that is close to an inner diameter of the tubular support member 1 and reduced diameter portions 44 and 46 that are spaced apart from the inner diameter of the tubular support member 1. In some instances, the enlarged diameter portion 42 may be positioned between the reduced diameter portions 44 and 46 of the mandrel 40. The mandrel 40 may be positioned within the tubular support member 1 with the reduced diameter portions 44 and 46 longitudinally positioned within the opposing end regions of the tubular support member 1 and the enlarged diameter portion 42 longitudinally positioned within the medial portion of the tubular support member 1 between the opposing end regions. A spray mechanism 48 sprays the polymeric material 22 towards the tubular support member 1. In some cases, the polymeric material 22 will span the cells 20 that overly the enlarged diameter portion 42 but will not span the cells 20 that overly the reduced diameter portions 44 and 46. In other words, the enlarged diameter portion 42, underlying the medial portion of the tubular support member 1 may impinge the sprayed polymeric material 22 to permit the polymeric material to span across the cells overlying the enlarged diameter portion 42, wherein the sprayed polymeric material 22 will pass through the cells 20 overlying the reduced diameter portions 44 and 46, and thus not span the cells 20 in this region. As can be seen in FIG. 7, the resulting endoprosthesis 50 includes a first region 52 in which the polymeric coating 22 spans the cells 20 that are within the first region 52 and a second region 54 in which the polymeric coating 22 does not span the cells 20 that are within the second region 54. As can be seen, the second region 54 is divided into a first area 54a near the first end 12 and a second area 54b near the second end 14.

Figure 8:
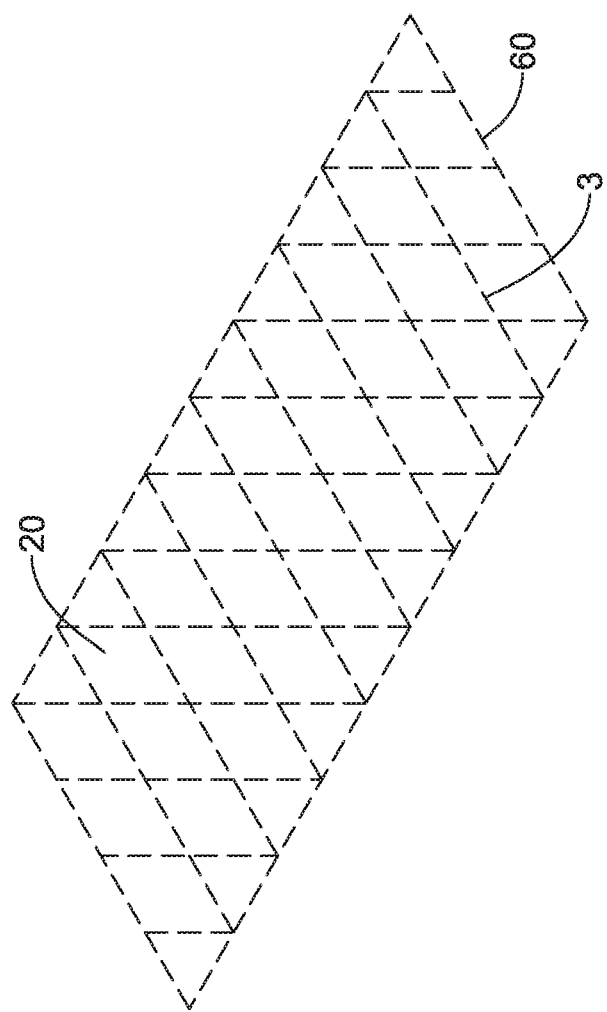
FIG. 8 is a schematic illustration of a system for removing portions of a coating from an endoprosthesis utilizing laser ablation in accordance with an embodiment of the disclosure.
Figure 9:
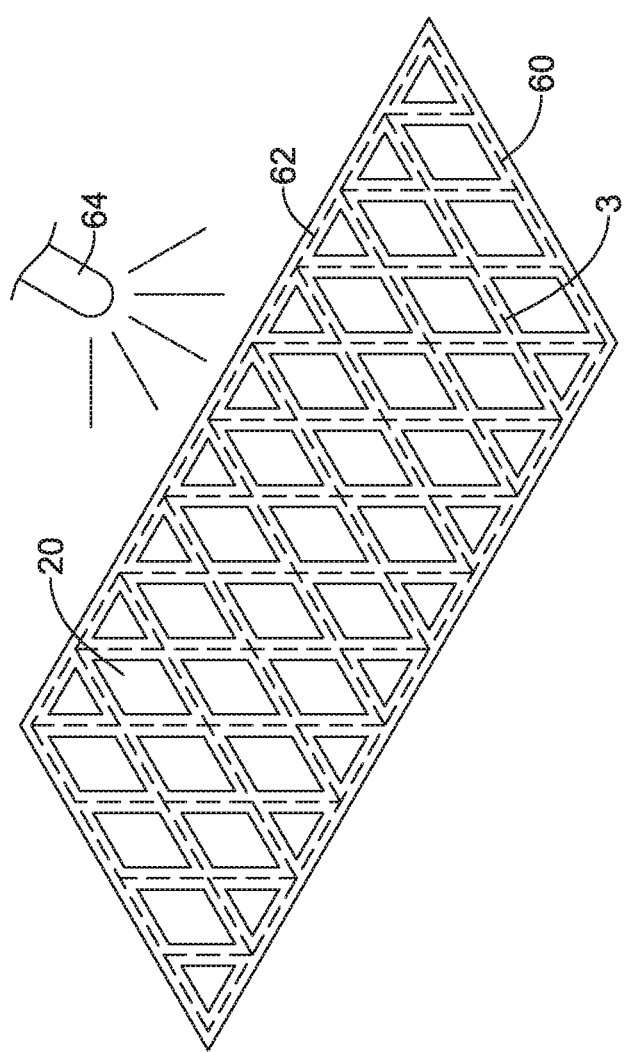
FIG. 9 is a schematic illustration of an endoprosthesis with a selectively removed coating via the system of FIG. 7, in accordance with an embodiment of the disclosure.
Figure 10:
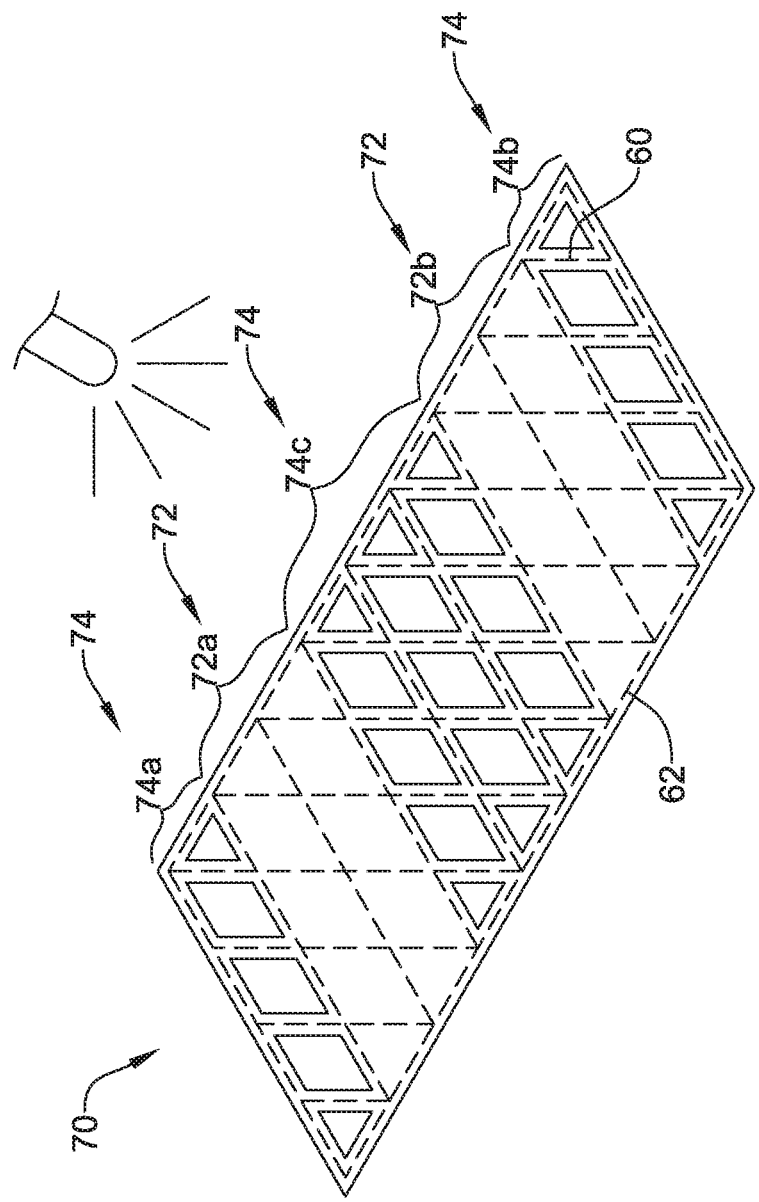
FIG. 10 is a schematic illustration of the tubular support member of FIG. 8, after a subsequent spray coating has covered some of the inter-strut spaces of the tubular support member in accordance with an embodiment of the disclosure.

FIGS. 8-10 illustrate another selective additional method. FIG. 8 shows a bare tubular support member 60 prior to the application of the polymeric material. In FIG. 9, a spray mechanism 64 is used to spray coat a polymeric coating 62 onto the individual struts 3 forming the tubular support member 60. In some cases, the polymeric coating 62 may cover the struts 3 but not span the cells 20 between adjacent struts 3. In some cases, spraying a solution having a relatively low concentration of the material forming the polymeric coating 62 may help ensure that the struts 3 are covered but that the cells 20 remain uncovered.

In FIG. 10, it can be seen that the polymeric coating 62 is spanning some of the cells 20 which have been covered. As illustrated, a resulting endoprosthesis 70 includes a first region 72, divided into a first area 72a and a second area 72b, in which the polymeric coating 62 spans the cells 20. The endoprosthesis 70 includes a second region 74, divided into a first area 74a, a second area 74b and a third area 74c, in which the polymeric coating 62 covers the struts 3 but does not span the cells 20 within the second region 74. In some cases, spraying a solution having a relatively high concentration of the material forming the polymeric coating 62 may help ensure that the cells 20 are covered.

Figure 11:
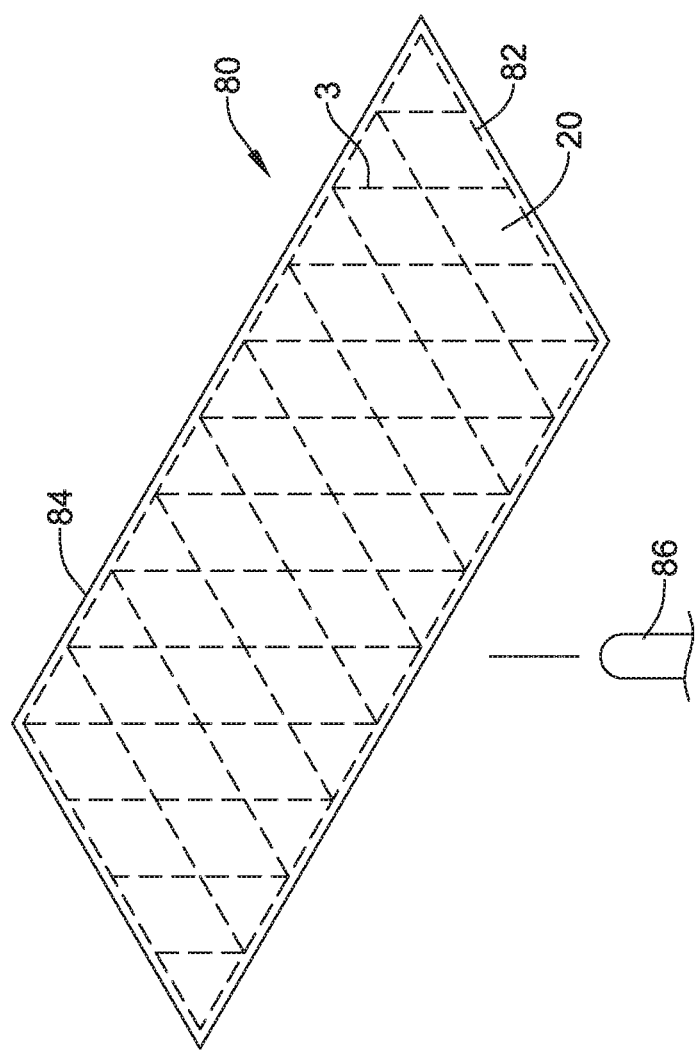
FIG. 11 is a schematic illustration of an uncoated tubular support member, before any coating, in accordance with an embodiment of the disclosure.
Figure 12:
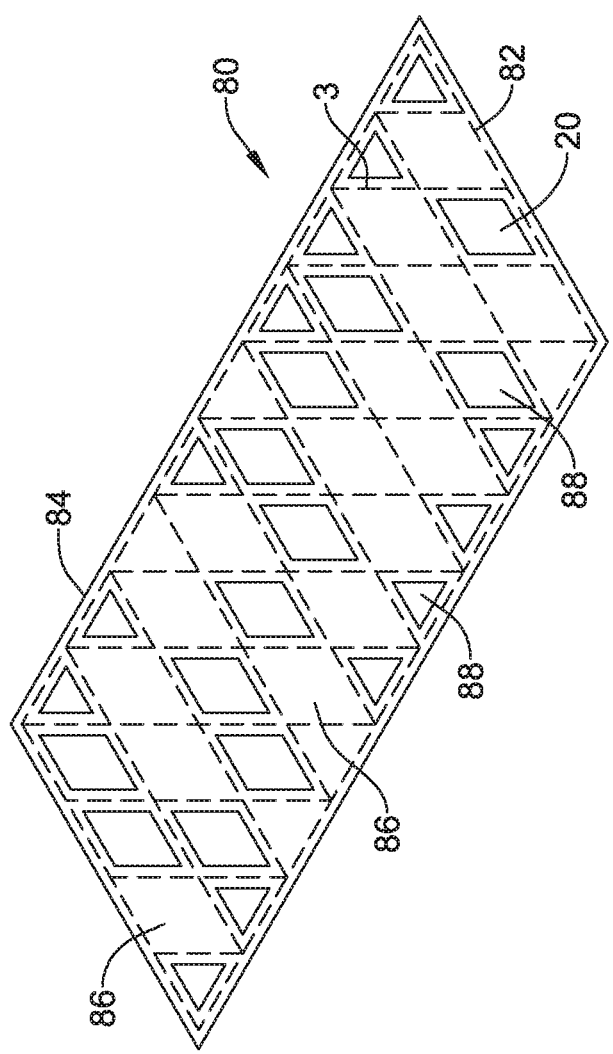
FIG. 12 is a schematic illustration of the tubular support member of FIG. 11, after an initial spray coating has covered the struts forming the tubular support member in accordance with an embodiment of the disclosure.

FIGS. 11 and 12 illustrate a selective removal method. FIG. 11 shows a fully coated endoprosthesis 80 in which a tubular support member 82 is fully or almost fully covered by a polymeric coating 84. The polymeric coating 84 may be formed using any desired technique, including but not limited to spray coating, dip coating, and the like. A laser assembly 86 may be used to remove at least some of the polymeric coating 84 that spans certain cells 20 while not removing the polymeric coating 84 spanning other cells 20. In some cases, the struts 3 forming the tubular support member 82 are covered with the polymeric coating 84, even after the laser assembly 86 is used to selectively remove polymeric material. In FIG. 12, the endoprosthesis 80 may be seen as having a number of cells 86 that are covered by the polymeric coating 84 and a number of cells 88 that are not covered by the polymeric coating 84. The struts 3 are covered by the polymeric coating 84.

Figure 13:
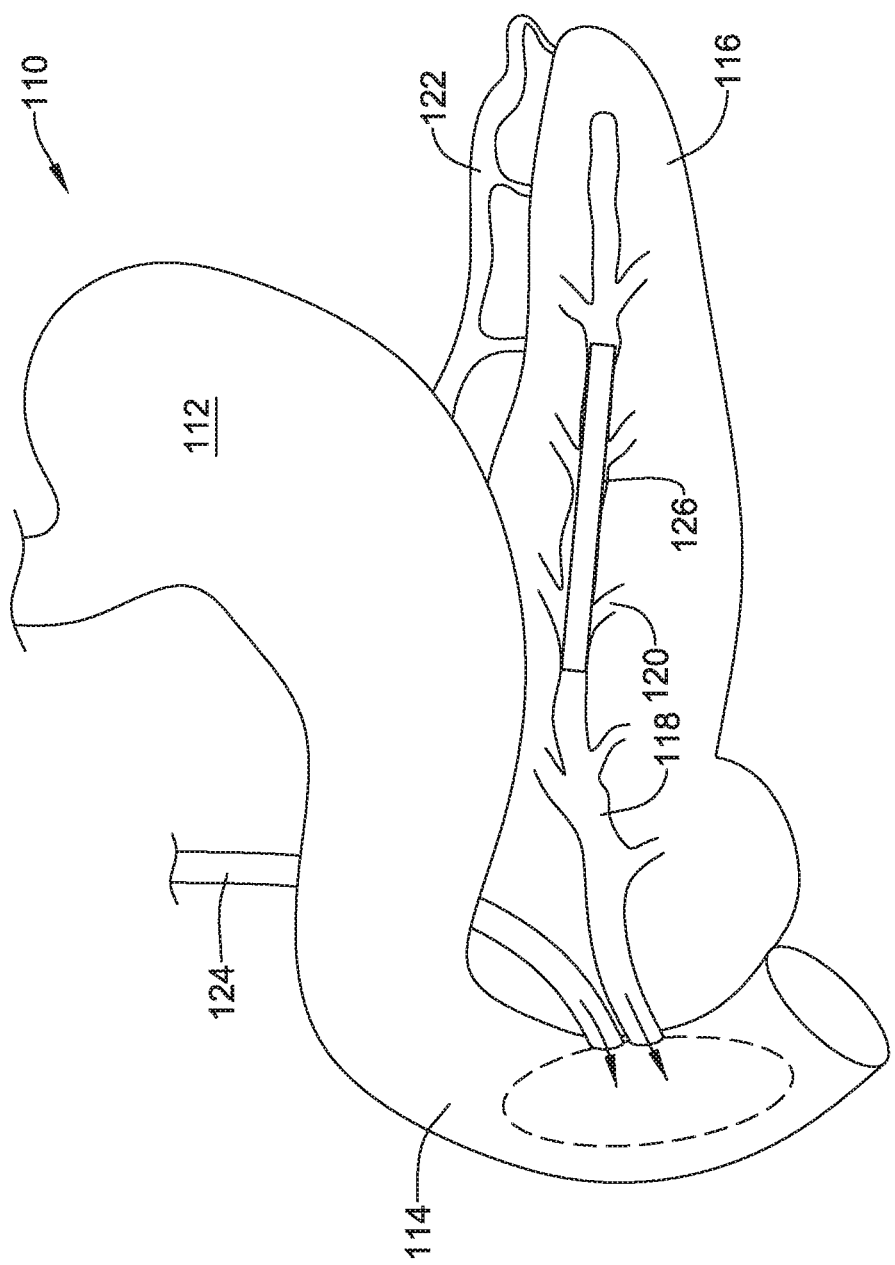
FIG. 13 is a schematic illustration of a portion of a patient's digestive system, including stomach and pancreas, illustrating placement of a pancreatic stent in accordance with an embodiment of the disclosure.

Once the endoprosthesis 10, 30, 32, 50, 80 has been formed as discussed herein, it may be implanted as desired. FIG. 13 provides an illustration of an endoprosthesis such as the endoprosthesis 10, 30, 32, 50, 80 being used as a pancreatic stent 120. FIG. 14 provides an illustration of an endoprosthesis such as the endoprosthesis 10, 30, 32, 50, 80 being used as an airway stent 23. It will be appreciated that these applications are illustrative only, as the endoprosthesis 10, 30, 32, 50, 80 described herein may be used in a variety of different body applications.

FIG. 13 provides a schematic illustration of a portion of a patient's digestive system 110, including a stomach 112 and duodenum 114. The patient's pancreas 11 is located just below the stomach 112 and is shown in cutaway fashion, illustrating the main pancreatic duct 13 extending through the pancreas 11 and terminating within the duodenum 114. The main pancreatic duct 13 is in fluid communication with a plurality of side branches 120 within the pancreas 11. While not expressly illustrated, the pancreas 11 includes duct cells that secrete aqueous $NaHCO_3$ solution into the main pancreatic duct 13. The pancreas 11 also includes Acinar cells that secrete digestive enzymes into the main pancreatic duct 13. While not illustrated, the pancreas 11 also includes Islets of Langerhans, which produce hormones such as insulin and glucagon. These hormones are excreted by the pancreas 11 into the blood stream, indicated as blood vessel 122, and the hormones then enter the stomach 112. A bile duct 124 extends from the liver (not shown) and also outputs into the duodenum 114.

In some instances, the main pancreatic duct 13 may become narrowed or inflamed, and there may be a desire to maintain the patency of the main pancreatic duct 13. In some embodiments, as illustrated, an endoprosthesis 126 may be deployed within the main pancreatic duct 13. The endoprosthesis 126 may be implanted in any suitable manner, including reaching the interior of the main pancreatic duct 13 from the interior of the duodenum 114. It will be appreciated that while the endoprosthesis 126 is illustrated and described herein as a pancreatic stent 126, the endoprosthesis 126 may be deployed in a variety of other bodily lumens, including but not limited to the vascular, urinary, biliary, tracheobronchial, esophageal or renal tracts. Although illustrated as a stent, the endoprosthesis 126 may be any of a number of devices that may be introduced endoscopically, subcutaneously, percutaneously or surgically to be positioned within an organ, tissue, or lumen, such as a heart, artery, vein, urethra, esophagus, trachea, bronchus, bile duct, or the like.

FIG. 14 provides a schematic illustration of the torso of a patient 210. The patient 210 includes a trachea 212 having a left main bronchus 214 and a right main bronchus 21 (relative to the patient's perspective). An endoprosthesis 23 may be seen in phantom, disposed within the right main bronchus 21 of the patient's trachea 212. It will be appreciated that this placement is merely for illustrative purposes, as the endoprosthesis 23 may be deployed elsewhere in the trachea 212 or even down into the bronchi (not illustrated). It will also be appreciated that while the endoprosthesis 23 is described herein as a pulmonary stent, the endoprosthesis 23 may be deployed in a variety of other bodily lumens, including but not limited to the vascular, urinary, biliary, tracheobronchial, esophageal or renal tracts. Although illustrated as a stent, the endoprosthesis 210 may be any of a number of devices that may be introduced endoscopically, subcutaneously, percutaneously or surgically to be positioned within an organ, tissue, or lumen, such as a heart, artery, vein, urethra, esophagus, trachea, bronchus, bile duct, or the like.

The polymer coating 22, 62, 84 may be formed of any suitable polymeric material. In some embodiments, the polymer coating 22, 62, 84 is formed of a biocompatible material such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like In some embodiments, the tubular support structure 1, 60, 82 may be formed from any desired material, such as a biocompatible material including biostable, bioabsorbable, biodegradable or bioerodible materials. For instance, the tubular support structure 1, 60, 82 may be formed of a metallic material. Some suitable metallic materials include, but are not necessarily limited to, stainless steel, tantalum, tungsten, nickel-titanium alloys such as those possessing shape memory properties commonly referred to as nitinol, nickel-chromium alloys, nickel-chromium-iron alloys, cobalt-chromium-nickel alloys, or other suitable metals, or combinations or alloys thereof.

In some embodiments, the tubular support structure 1, 60, 82 may include one or more metals. Some examples of suitable metals and metal alloys include stainless steel, such as 304V, 304L, and 31LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Those skilled in the art will recognize that aspects of the present disclosure may be manifested in a variety of forms other than the specific embodiments described and contemplated herein. Accordingly, departure in form and detail may be made without departing from the scope of the present disclosure as described in the appended claims.

What is claimed is:

1. A medical stent comprising:
a tubular support structure including a plurality of struts, the plurality of struts defining a plurality of cells disposed between the plurality of struts; and
a polymeric coating disposed over the tubular support structure such that a first portion of the plurality of cells are closed by the polymeric coating in a first region of the tubular support structure and a second portion of the plurality of cells in a second region of the tubular support structure remain open to fluid flow or tissue ingrowth therethrough;
wherein the struts in the first region of the tubular support structure and the struts in the second region of the tubular support structure are at least partially covered by the polymeric coating;
wherein the polymeric coating extends laterally beyond the struts and partially into each of the plurality of open cells in the second region.

2. The medical stent of claim 1, wherein the struts in the first region of the tubular support structure and the struts in the second region of the tubular support structure are encapsulated by the polymeric coating.

3. The medical stent of claim 1, wherein the polymeric coating is formed by covering the tubular support structure with the polymeric coating and subsequently removing part of the polymeric coating spanning one or more of the plurality of cells within the second region of the tubular support structure.

4. The medical stent of claim 1, wherein the polymeric coating is formed by encapsulating the plurality of struts and subsequently coating at least one or more of the plurality of cells within the first region of the tubular support structure.

5. The medical stent of claim 1, wherein the polymeric coating is formed by placing the tubular support structure over a mandrel and then spray coating the tubular support structure, wherein the mandrel includes raised portions contacting the tubular support structure within the first region and portions spaced from the tubular support structure within the second region.

6. The medical stent of claim 1, wherein the first region of the tubular support structure, in which the first portion of the plurality of cells are covered by the polymeric coating, includes one or more distinct areas of the tubular support structure.

7. The medical stent of claim 1, wherein the second region of the tubular support structure, in which the second portion of the plurality of cells remain open to fluid flow or tissue ingrowth therethrough, includes one or more distinct areas of the tubular support structure.

8. The medical stent of claim 1, wherein the second region of the tubular support structure, in which the second portion of the plurality of cells remain open to fluid flow or tissue ingrowth therethrough, includes a first area of cells open to fluid flow or tissue ingrowth and a second area of cells open to fluid flow or tissue ingrowth, with the first region positioned between the first and second areas of cells open to fluid flow or tissue ingrowth.

9. The medical stent of claim 1, wherein the polymeric coating comprises polyurethane or silicone.

10. The medical stent of claim 1, wherein the medical stent is a pulmonary stent.

11. The medical stent of claim 1, wherein the medical stent is an esophageal stent.

12. The medical stent of claim 1, wherein the medical stent is a pancreatic stent.

13. A medical stent comprising:
a metallic support structure including a plurality of struts defining inter-strut spaces therebetween, the plurality of struts together defining a shape of the metallic support structure; and
a cushioning material coated on at least some of the plurality of struts;
wherein the cushioning material extends laterally beyond the struts and partially into at least some of the inter-strut spaces adjacent struts bearing the cushioning material such that the at least some inter-strut spaces are open to fluid flow or tissue ingrowth therethrough.

14. The medical stent of claim 13, further comprising a polymeric layer completely spanning at least some of the inter-strut spaces that are different inter-strut spaces than those that are open to fluid flow or tissue ingrowth.

15. The medical stent of claim 14, wherein the cushioning material comprises a polymeric material, and the polymeric layer comprises the same polymeric material.

16. The medical stent of claim 13, wherein the cushioning material comprises polyurethane or silicone.

17. A medical stent comprising:
a tubular support structure including a plurality of struts, the plurality of struts defining a plurality of cells disposed between the plurality of struts, each of the cells extending from an outer surface of the tubular support structure to an inner surface of the tubular support structure; and a polymeric coating coated onto the plurality of struts of the tubular support structure such that a first portion of the plurality of cells are closed by the polymeric coating in a first region of the tubular support structure and a second portion of the plurality of cells in a second region of the tubular support structure remain open to fluid flow or tissue ingrowth therethrough;

wherein struts coated with the polymeric coating extend between adjacent open cells in the second region of the tubular support structure.

18. The medical stent of claim 17, wherein the polymeric coating extends laterally beyond the struts coated with the polymeric coating and partially into the open cells in the second region.

19. The medical stent of claim 1, wherein struts covered with the polymeric coating extend between adjacent open cells in the second region of the tubular support structure.

20. The medical stent of claim 13, wherein struts having the cushioning material coated thereon extend between adjacent inter-strut spaces open to fluid flow or tissue ingrowth.

* * * * *